USD05190942A

United States Patent [19]

Poss

[11] Patent Number: 5,190,942

[45] Date of Patent: Mar. 2, 1993

[54] BENZOXAZOLE AND RELATED HETEROCYCLIC SUBSTITUTED IMIDAZOLE AND BENZIMIDAZOLE DERIVATIVES

[75] Inventor: Michael A. Poss, Lawrenceville, N.J.

[73] Assignee: E. R. Squibb & Sons, Inc., Princeton, N.J.

[21] Appl. No.: 688,768

[22] Filed: Apr. 22, 1991

[51] Int. Cl.$^5$ .............. A61K 31/535; A61K 31/415; C07D 263/57; C07D 277/62; C07D 403/02; C07D 233/91; C07D 233/54

[52] U.S. Cl. .................. 514/235.8; 514/255; 514/326; 514/397; 514/398; 514/399; 514/400; 544/132; 544/370; 546/210; 548/224; 548/113; 548/179; 548/180; 548/255; 548/260; 548/338.1; 548/340.1; 548/342.5; 548/341.5; 548/305.7; 548/305.1; 548/306.1; 548/312.1; 548/311.4; 548/314.4; 548/314.7; 548/337.1; 548/329.1; 548/330.1; 548/330.5; 548/328.5; 548/342.1; 548/341.1; 548/343.1; 548/346.1; 548/345.1; 548/333.5

[58] Field of Search .............. 548/224, 327, 328, 339, 548/340, 342, 255, 260, 179, 180, 113; 514/397, 398, 399, 400, 235.8, 255, 326; 544/132, 370; 546/210

[56] References Cited

U.S. PATENT DOCUMENTS

| | | | |
|---|---|---|---|
| 4,340,598 | 7/1982 | Furukawa et al. | 424/273 |
| 4,355,040 | 10/1982 | Furukawa et al. | 424/273 |
| 4,582,847 | 4/1985 | Furukawa et al. | 514/400 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234 |

FOREIGN PATENT DOCUMENTS

| | | | |
|---|---|---|---|
| 253310 | 9/1987 | European Pat. Off. | 424/273 |
| 323841 | 5/1989 | European Pat. Off. | 548/252 |
| 324377 | 5/1989 | European Pat. Off. | 548/252 |

*Primary Examiner*—Mary C. Lee
*Assistant Examiner*—Joseph K. McKane
*Attorney, Agent, or Firm*—Ellen K. Park

[57] ABSTRACT

Novel compounds are disclosed having the formula

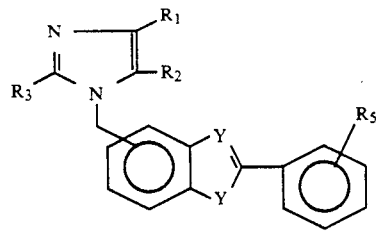

wherein X, Y, $R_1$, $R_2$, $R_3$, $R_4$, and $R_5$ are as defined herein. These compounds inhibit the action of angiotensin II and are useful, therefore, for example, as antihypertensive agents.

13 Claims, No Drawings

BENZOXAZOLE AND RELATED HETEROCYCLIC SUBSTITUTED IMIDAZOLE AND BENZIMIDAZOLE DERIVATIVES

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

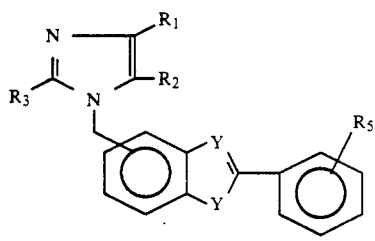

and pharmaceutically acceptable salts thereof;

where X is

or N;

Y is O, S, $NR_6$, or $CR_6R_6'$ $R_1$ is hydrogen, halogen, $-NO_2$, $-CF_3$ or $-CN$;

$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazolyl-1-yl; $-(CH_2)_m$-1,2,3-triazolyl optionally substituted with one or two groups selected from $CO_2R_7$ or alkyl of 1 to 4 carbon atoms;

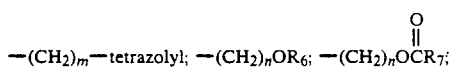

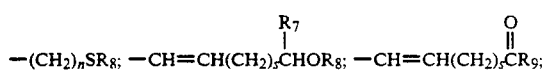

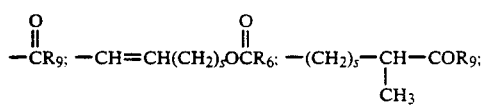

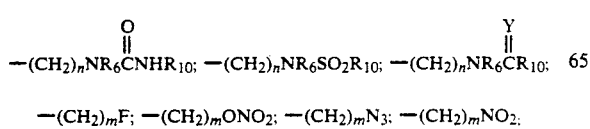

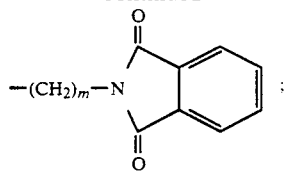

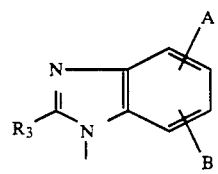

or $R_1$ and $R_2$ taken together with the carbon atoms of the imidazole nucleus to which they are attached can form a benzimidazole shown as

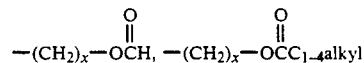

wherein A can be hydrogen, alkyl, $C_xF_{2x+1}$, $C_6F_5$, halogen, $C_{1-6}$alkoxy, $-(CH_2)_xOH$, $-(CH_2)_x-OC_{1-4}$alkyl, $-(CH_2)_x-\overset{O}{\overset{\|}{O}}CH$, $-(CH_2)_x-\overset{O}{\overset{\|}{O}}CC_{1-4}$alkyl or $-COR_9$ and B can be hydrogen, alkyl, $C_xF_{2x+1}$, $C_6F_5$, halogen or $C_{1-6}$alkoxy;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; $-(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ is hydrogen, alkyl, aryl, cycloalkyl, aralkyl, $-COOR_7$, or $-CONR_{14}R_{15}$;

$R_5$ is hydrogen, $-COOH$, $-NHSO_2CF_3$,

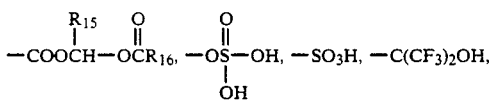

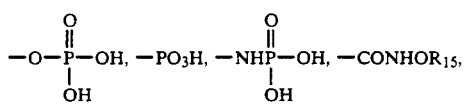

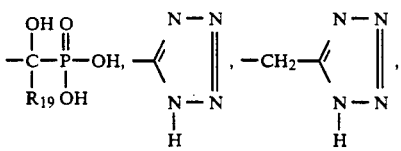

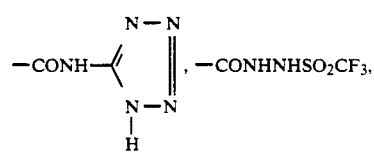

-continued

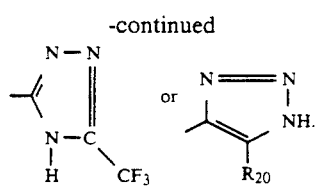

$R_6$ and $R_6'$ are independently selected from H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{13}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R_{11}$ is H, alkyl of 1 to 6 carbon atoms, cycloalkyl of 3 to 6 carbon atoms, phenyl or benzyl;

$R_{12}$ and $R_{13}$ independently are H, alkyl of 1 to 4 carbon atoms, phenyl, benzyl, α-methylbenzyl, or taken together form a ring of the formula

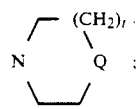

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl, $-NR_{17}R_{18}$ or

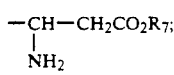

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$s is H, $C_{1-5}$alkyl, phenyl;

$R_{20}$ is $-CN$, $-NO_2$ or $-CO_2R_7$;

Y=O or S;

Z=O, $NR_6$ or S;

m is 1-5;

n is 1-10;

p is 0-3;

q is 2-3;

r is 0-2;

s is 0-5;

t is 0 or 1; and x is 1 to 6.

DETAILED DESCRIPTION OF THE INVENTION

In its broadest aspects the present invention relates to the compounds of formula I and to pharmaceutical compositions and methods employing such compounds.

The term "aryl", as used throughout the specification either by itself or as part of a larger group, refers to phenyl or phenyl substituted with one or more groups selected from halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

To prepare the compounds of formula I where X is $-N-$ and Y is $-O-$ and where $R_1$ and $R_2$ do not form a benzene ring, a compound of the formula

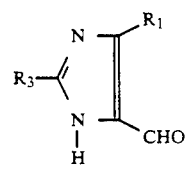

II is coupled with a compound of the formula

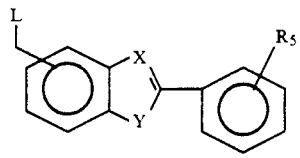

III wherein L is a leaving group such as a halogen, in the presence of a base, e.g., potassium hexamethyldisilazane, in solvents such as tetrahydrofuran and dimethylformamide, to provide the compound

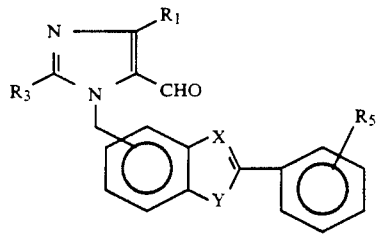

IV

Aldehyde IV can thereafter be treated with a reducing agent, such as sodium borohydride, in a solvent such as ethanol to provide

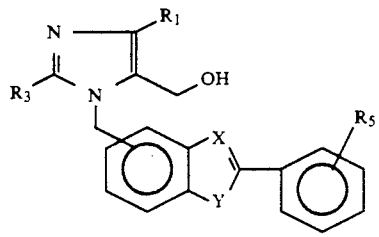

Ia that is, compounds of formula I wherein $R_2$ is $-CH_2-OH$. Using known techniques, compounds of formula I where $R_2$ is other than $-CH_2OH$ can be prepared from compound Ia. For example, alcohols of formula Ia can be alkylated or acylated to provide the corresponding products of formula I. Alternatively, compounds of formula I can be prepared from IV by Wittig homologation of the aldehyde.

The imidazole aldehyde II can be prepared by treating a compound of the formula

V in pyridine, with an oxidizing agent, e.g., manganese oxide.

Compounds of formula III can be prepared by coupling a compound of the formula

VI with a compound of the formula

VII where X is halo, e.g., bromine, for example, in the presence of a coupling agent such as tetrakis(triphenylphosphine)palladium to provide compounds of the formula

VIII

A leaving group, L, for example, a halogen such as bromide, can be added by known methodology to provide compounds of formula III.

Compounds of formula I wherein X is $$\begin{matrix} & R_4 \\ & | \\ - & C - \end{matrix}$$

and Y is oxygen can be prepared by reacting a compound of the formula

IX with a compound of the formula

X in the presence of a coupling agent such as tetrakis(triphenylphosphine)palladium and in a solvent such as tetrahydrofuran provide a compound of the formula

XI

Compound XI can thereafter be treated with N-bromosuccinimide and a radical initiator, e.g., 2,2'-azobisisobutyronitrile, in a solvent, e.g., carbon tetrachloride, to provide a compound of the formula

XII

Intermediate XII can be coupled with the aldehyde of formula II, in the presence of a base such as t-butoxide in a solvent such as dimethylformamide to provide

XIII

The aldehyde XIII can be treated as the aldehyde IV above to provide

XIV

Compound XIV can then be reacted with a base such as LiOH, to provide compounds of formula I where X is $$\begin{matrix} & R_4 \\ & | \\ - & C - \end{matrix},$$

Y is oxygen and $R_5$ is $CO_2H$.

Compounds of formula I where X is nitrogen and Y is oxygen can be prepared by reacting a compound of formula

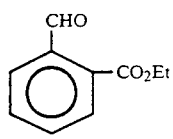
XV with a compound of the formula

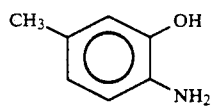
XVI in an organic solvent in the presence of an oxidizing agent, such as silver oxide to form a compound of the formula

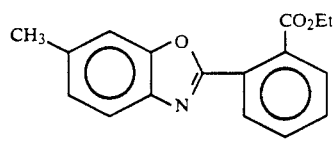
XIa

Compound XIa can thereafter be treated with N-bromosuccinimide and a radical initiator, e.g., 2,2'-azobisisobutyronitrile, in a solvent, e.g., carbon tetrachloride, to provide a compound of the formula

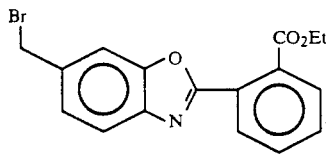
XIIa

Intermediate XIIa can be coupled with the aldehyde of formula II in the presence of a base such as potassium hexamethyldisilazane in a solvent such as tetrahydrofuran and dimethylformamide to provide

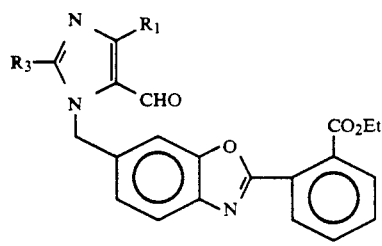
XIIIa

The aldehyde XIIIa can be treated with a base such as potassium hexamethyldisilazane in a solvent such as methanol to provide a compound of formula

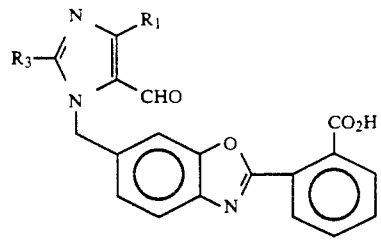
XVII

Compounds of formula XV can be formed by reacting a compound of formula

XVa with ethyl iodide in the presence of a base such as sodium hydrogen carbonate in a solvent such as dimethylformamide.

The compounds of formula I wherein $R_1$ and $R_2$ together with the imidazole nucleus to which they are attached form a benzimidazole can be prepared using the methodology in U.S. Pat. No. 4,880,804.

Preferred compounds of the present invention are those wherein $R_1$ is hydrogen or halogen;
$R_2$ is —CH$_2$OH or —CHO;
$R_3$ is $C_{2-10}$alkyl or $C_{3-10}$alkenyl;
$R_4$ is H or —COOH;
$R_5$ is ortho-tetrazole or COOH;
X is —N— and Y is —O— or X is $$\begin{array}{c} R_4 \\ | \\ -C- \end{array}$$

and Y is —O—;

Most preferred are compounds of formula I wherein
$R_1$ is chloro;
$R_2$ is —CHO;
$R_3$ is n-butyl;
connection from the imidazole portion is via the 6-position of the benzoxazole;
X is N;
Y is O; and
$R_5$ is ortho-COOH.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE

2-[6-[(2-Butyl-4-chloro-5-formyl-1H-imidazol-1-yl) methyl]-2-benzoxazolyl]benzoic acid, monopotassium salt A. 2-formylbenzoic acid, ethyl ester 2-Carboxybenzaldehyde (2.018g, 13.4 mmol, 1.0 eq.) was combined with sodium bicarbonate (2.258 g, 26.9 mmol, 2.0 eq.) and iodoethane (2.15 ml, 26.9 mmol, 2.0 eq.) in dimethylformamide (13.4 ml, 1M) and stirred at room temperature for 16 hours. The reaction was diluted with water (25 ml) and extracted with ether: hexane (1:1, 3X20 ml). The combined organic extracts were washed with aqueous 10% sodium bisulfite (1X25 ml), water (1X25 ml) and aqueous saturated sodium chloride (1X25 ml), dried over sodium sulfate, filtered through magnesium sulfate and concentrated. The residue was chromatographed on Merck silica gel (20 g) eluting with hexane: ether (14:1) to provide the title A compound (1.485 g).

B. 2-(6-methyl-2-benzoxazolyl) benzoic acid, ethyl ester

The title A Compound (92.9 mg, 0.521 mmol, 1.0 eq.) was combined with 6-amino-meta-cresol (64.2 mg, 0.521 mmol, 1.0 eq.) and sodium sulfate (259 mg, 1.82 mmol, 3.5 eq.) in benzene (1.04 ml, 0.5M). The reaction was stirred at room temperature for 16 hours, filtered through a small pad of magnesium sulfate and concentrated. The residue was dissolved in methylene chloride (5.2 ml, 0.1M), treated with silver oxide (145 mg, 0.626 mmol, 1.2 eq.), and stirred at room temperature for 4 days. The reaction was then filtered through celite and concentrated. The residue was chromatographed on Merck silica gel (10 g) eluting with ether: hexane (1:8) followed by (1:5) to give the title B compound (108 mg).

C. 2-[6-(Bromomethyl)-2-benzoxazolyl]benzoic acid, ethyl ester

The title B compound (60.7mg, 0.216mmol, 1.0 eq.) was combined with N-bromosuccinimide (38.4 mg, 0.216 mmol, 1.0 eq.) and azobisisobutyronitrile (1.8 mg, 3% by weight) in carbon tetrachloride (2.16 ml, 0.1M) and heated at reflux for 2 hours. The reaction was then cooled to room temperature, filtered through magnesium sulfate and concentrated. The residue was chromatographed on Merck silica gel (5 g) eluting with ether:hexane (1:7) followed by (1:5) to furnish the title C Compound (81.5 mg).

D. Pentanamidic acid, ethyl ester hydrochloride

Hydrogen chloride gas was bubbled into a tared solution of valeronitrile (92.0 g, 1.08 mole) in absolute ethanol (64 ml, 1.08 mole) in a 1-liter round bottomed flask cooled to 0° C. The flask was weighed periodically and hydrogen chloride bubbling was continued until the weight gain was greater than 39 g (1.08 mole). The mixture was then stoppered and stored at 0° C. for 6 days. Ether (650 ml) was then added (cold) and the mixture was stored at −30° C. for 24 hours. The resulting solid was collected on a buchner funnel, transferred quickly to a large beaker, triturated quickly with cold ether, and collected again on a buchner funnel. The solid was then dried in vacuum to give the title D compound as a free flowing white solid (95 g).

E. 2-Butyl-1H-imidazole-4-methanol

A 300 ml stainless steel Parr pressure bomb containing dihydroxyacetone dimer (5.0 g, 55 mmol) was cooled in a dry ice bath for one hour. During the cooling period, the bomb lid was set on top of the bomb and held in place by applying a light vacuum; the associated hardware for holding the lid in place under pressure was not cooled (to facilitate handling later). When the bomb was sufficiently cooled, liquid ammonia was condensed into a 250 ml three neck flask fitted with a dry ice condensor at −78° C. The cold bomb was then opened by releasing the vacuum, the title D compound (9.1 g, 55 mmol) was added, followed immediately by liquid ammonia from the 250 ml flask (approx. 55 ml of ammonia was added). The bomb was sealed using the appropriate hardware, removed from the dry ice bath, and allowed to warm to room temperature. The bomb was then immersed about half way in an oil bath and heated to 75° C. for three hours, during which the pressure rose to 320 psi. Heating was then discontinued and the pressure relief valve was slowly opened and the ammonia was allowed to evaporate (evaporative cooling helped cool the bomb). When the pressure was completely equilibrated, the bomb was opened and its contents were transferred to a conventional flask using acetonitrile to wash the residue out. The mixture was concentrated in vacuo and the residue was purified by flash chromatography on silica gel (1500 g), eluting with 80:20:1 chloroform:methanol:ammonium hydroxide. Fractions containing the major product ($R_f$ 0.5) were combined and concentrated. The residue was then crystallized from acetonitrile (200 ml) to give the title E compound as a white crystalline solid, mp 92°-93° C. (5.74 g).

F. 2-Butyl-4 chloro-1H-imidazole-5-carboxaldehyde

A solution of the title E compound in a mixture of absolute ethanol (40 ml) and terahydrofuran (80 ml) was cooled in an ice bath. To the cold solution was added N-chlorosuccinimide (5.9 g, 44.4 mmol) in small portions over 60 minutes. The resulting mixture was stirred for 30 minutes in the ice bath, then for 30 minutes at 25° C., after which a starch-iodine test was negative. The mixture was concentrated in vacuo to give a residue. The residue was triturated with ether (400 ml) to give a tan solid. The mother liquor from trituration was concentrated and the residue was re-triturated with ether (40 ml) to give more of the tan solid. The solids were combined, dissolved in pyridine (200 ml), and warmed to 100° C. Maganese dioxide (20 g) was added to the warm solution and the resulting black mixture was stirred at 100° C. for one hour. The hot solution was filtered and concentrated. The residue was purified by chromatography on silica gel (500 g), eluting with 3:1 hexane:ethyl acetate, to give a major product having $R_f$ 0.4. The product was triturated with petroleum ether to give the title F compound as a white crystalline solid, mp 96°-97° C.

$C_8H_{11}ClN_2O$, Calculated: % C 51.48, % H 5.94, % N 15.01 % Cl 19.00, Found: % C 51.29, % H 5.80, % N 14.95, % Cl 19.36.

m.p.96°-97° C.

G. 2-[6-[(2-Butyl-4-chloro-5-formyl 1H-imidazol-1-yl)methyl]-2-benzoxazolyl]-benzoic acid, ethyl ester The title F compound (41.3mg, 0.221 mmol, 1.1 eq.) was dissolved in tetrahydrofuran (0.51 ml, 0.4M) and dimethylformamide (0.17 ml, 1.2M), cooled to 0° C., and treated with potassium hexamethyldisilylazide (0.31 ml, 0.232 mmol, 1.15 eq., 0.75M in toluene). After 10 minutes, the title C compound (72.5 mg. 0.201 mmol, 1.0 eq.) in tetrahydrofuran (0.20 ml, 1M) was added. The reaction was then warmed to room temperature and stirred for 16 hours. The mixture was quenched with aqueous saturated ammonium chloride and extracted three times with ethyl acetate. The organic extracts were filtered through magnesium sulfate and concentrated. The residue was chromatographed on Merck silica gel (5 g) eluting with ether: hexane (2:3) followed by (1:1) to give the title G compound (58.5 mg).

H. 2-[6-[(2-Butyl-4-chloro-5-formyl-1H-imidazol-1-yl)methyl]-2-benzoxazolyl]benzoic acid, monopotassium salt.

The title G compound (56.3 mg, 0.121 mmol, 1.0 eq.) was dissolved in methanol (2.0 ml, 0.06M) and treated at room temperature with aqueous 1N potassium hydroxide (1.0 ml, 1.0 mmol, 8.3 eq.). After 7 hours, the reaction was concentrated. The residue was chromatographed on HP-20 resin (10 g) eluting with water (100 ml), 1% acetone in water (100 ml), 3% acetone in water (100 ml , 5% acetone in water (100 ml), 10% acetone in water (50 ml) and 20% acetone in water (50 ml). The product eluted off the column with 20% acetone in water. The fractions were concentrated to a volume of ~25 ml and lyophilized. The product was dissolved in water (10 ml), filtered through a polycarbonate membrane and lyophilized to furnish the title H compound (42.5 mg).

$C_{23}H_{19}ClN_3O_4.K.1.4 H_2O$ Calculated: % C 55.12, % H 4.38, % N 8.38 % Cl 7.07, Found: % C 55.15, % H 4.39, % N 8.05 % Cl 7.07.

m.p. 190° C. (decomposition)

TLC: $R_f$=0.64, silica gel, Ethyl Acetate: Pyridine: Acetic Acid: Water (20:1:1:0.5), cobalt stain.

What is claimed is:

1. A compound of the formula

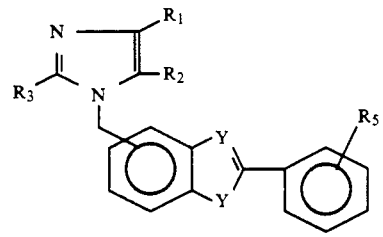

and pharmaceutically acceptable salts thereof;
where X is

or N;

Y is O, S, $NR_6$, or $CR_6R_6'$;

$R_1$ is hydrogen, halogen, $-NO_2$, $-CF_3$ or $-CN$;

$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2R_7$ or alkyl of 1 to 4 carbon atoms;

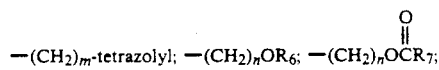

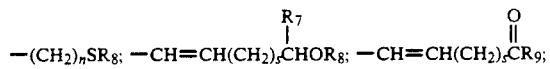

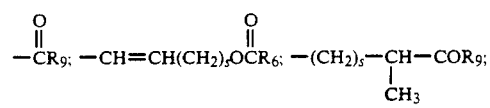

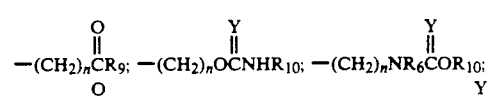

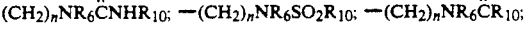

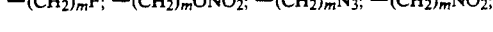

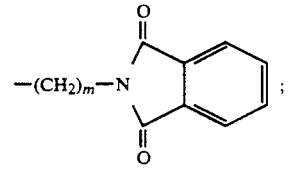

or $R_1$ and $R_2$ taken together with the carbon atoms of the imidazole nucleus to which they are attached can form a benzimidazole shown as

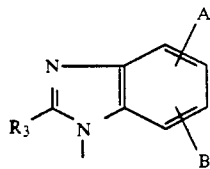

wherein A can be hydrogen, alkyl, $C_xF_{2x+1}$, $C_6F_5$, halogen, $C_{1-6}$alkoxy, $-(CH_2)_xOH$, $-(CH_2)_x-OC_{1-4}$alkyl,

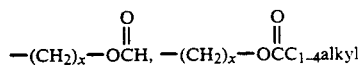

or $-COR_9$ and B can be hydrogen, alkyl, $C_xF_{2x+1}$, $C_6F_5$, halogen or $C_{1-6}$alkoxy;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ is hydrogen, alkyl, aryl, cycloalkyl, aralkyl, $-COOR_7$ or $-CONR_{14}R_{15}$;

$R_5$ is hydrogen,

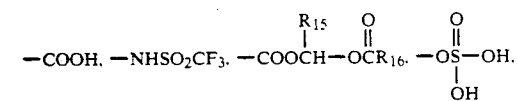

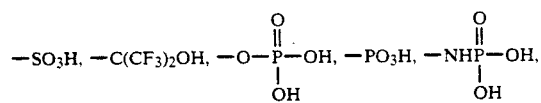

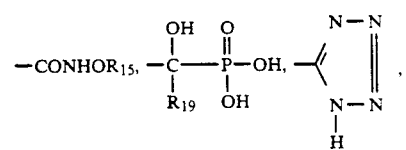

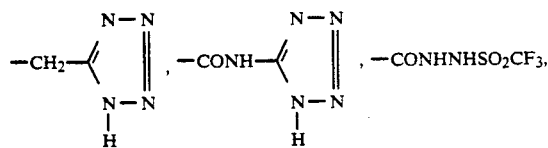

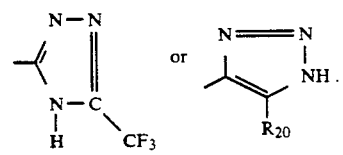

$R_6$ and $R_6'$ are independently selected from H, alkyl of 1 to 6 carbon atoms, cycloalkyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, $(CH_2)_pC_6H_5$, $OR_{11}$ or $NR_{12}R_{12}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R_{11}$ is H, alkyl of 1 to 6 carbon atoms, cycloalkyl of 3 to 6 carbon atoms, phenyl or benzyl;

$R_{12}$ and $R_{13}$ independently are H, alkyl of 1 to 4 carbon atoms, phenyl, benzyl, α-methylbenzyl, or taken together form a ring of the formula

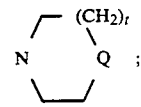

Q is $NR_{14}$, O or $CH_2$;

$R_{14}$ and $R_{15}$ are independently H, alkyl, aryl, aralkyl or cycloalkyl;

$R_{16}$ is $C_{1-6}$alkyl, $-NR_{17}R_{18}$ or

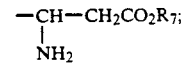

$R_{17}$ and $R_{18}$ are independently H, $C_{1-6}$alkyl, benzyl or taken together are 3 to 6 carbon atoms forming a 4- to 7-membered ring with the nitrogen atom to which they are attached;

$R_{19}$ is H, $C_{1-5}$alkyl, phenyl;

$R_{20}$ is $-CN$, $-NO_2$ or $-CO_2R_7$;

Y=O or S;

Z=O, $NR_6$ or S;

m is 1-5;

n is 1-10;

p is 0-3;

q is 2-3;

r is 0-2;

s is 0-5;

t is 0 or 1; and x is 1-6.

2. A compound of the formula

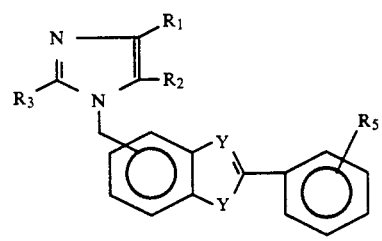

or pharmaceutically acceptable salts thereof;
where X is N;
Y is O;
$R_1$ is hydrogen, halogen, $-NO_2$, $-CF_3$ or $-CN$;
$R_2$ is hydrogen, $-CN$, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$- imidazolyl-1-yl; —(CH$_2$)$_m$-1,2,3-triazolyl optionally substituted with one or two groups selected from —CO$_2$R$_7$ or alkyl of 1 to 4 carbon atoms; —(CH$_2$)$_m$—tetrazolyl;

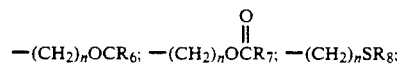

—(CH$_2$)$_n$OCR$_6$; —(CH$_2$)$_n$OCR$_7$; —(CH$_2$)$_n$SR$_8$;

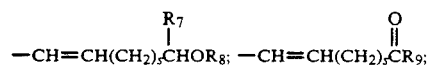

—CH=CH(CH$_2$)$_s$CHOR$_8$; —CH=CH(CH$_2$)$_s$CR$_9$;

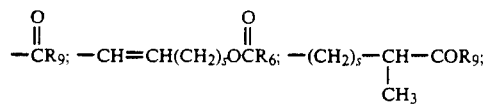

—CR$_9$; —CH=CH(CH$_2$)$_s$OCR$_6$; —(CH$_2$)$_s$—CH—COR$_9$;
$\qquad\qquad\qquad\qquad\qquad\qquad\qquad\qquad\qquad$ |
$\qquad\qquad\qquad\qquad\qquad\qquad\qquad\qquad\qquad$ CH$_3$

—(CH$_2$)$_n$CR$_9$; —(CH$_2$)$_n$OCNHR$_{10}$; —(CH$_2$)$_n$NR$_6$COR$_{10}$;

—(CH$_2$)$_n$NR$_6$CNHR$_{10}$; —(CH$_2$)$_n$NR$_6$SO$_2$R$_{10}$; —(CH$_2$)$_n$NR$_6$CR$_{10}$;

—(CH$_2$)$_m$F; —(CH$_2$)$_m$ONO$_2$; —(CH$_2$)$_m$N$_3$; —(CH$_2$)$_m$NO$_2$;

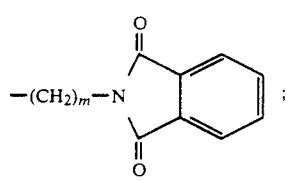

R$_3$ is alkyl of 2 to 10 carbon atoms, alkenyl or alkynyl of 3 to 10 carbon atoms or the same groups substituted with F or —CO$_2$R$_7$; cycloalkyl of 3 to 8 carbon atoms, cycloalkylalkyl of 4 to 10 carbon atoms; cycloalkylalkenyl or cycloalkylalkynyl of 5 to 10 carbon atoms; (CH$_2$)$_s$Z(CH$_2$)$_m$R' (wherein R' is hydrogen, C$_{1-6}$alkyl, C$_{3-6}$cycloalkyl, C$_{2-4}$alkenyl or C$_{2-4}$alkynyl) optionally substituted with F or —CO$_2$R$_7$; benzyl or benzyl substituted on the phenyl ring with 1 or 2 halogens, alkoxy of 1 to 4 carbon atoms, alkyl of 1 to 4 carbon atoms or nitro;
R$_5$ is hydrogen, —COOH, —NHSO$_2$CF$_3$,

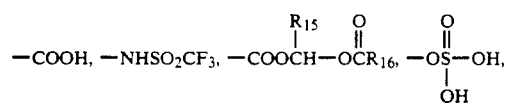

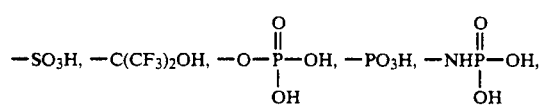

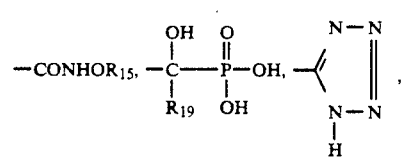

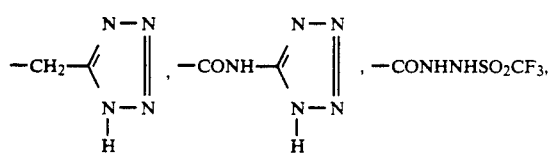

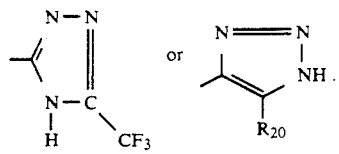

R$_6$ is hydrogen, alkyl of 1 to 6 carbon atoms, cycloalkyl of 3 to 6 carbon atoms, phenyl or benzyl;
R$_7$ is hydrogen, alkyl or perfluoroalkyl of 1 to 8 carbon atoms, cycloalkyl of 3 to 6 carbon atoms, phenyl or benzyl;
R$_8$ is hydrogen, alkyl of 1 to 6 carbon atoms, cycloalkyl of 3 to 6 carbon atoms, phenyl, benzyl, acyl of 1 to 4 carbon atoms or phenacyl;
R$_9$ is hydrogen, alkyl of 1 to 6 carbon atoms, cycloalkyl of 3 to 6 carbon atoms, —(CH$_2$)$_p$C$_6$H$_5$, —OR$_{11}$ or —NR$_{12}$R$_{13}$;
R$_{10}$ is alkyl of 1 to 6 carbon atoms or perfluoroalkyl of 1 to 6 carbon atoms, 1-adamantyl, 1-naphthyl, 1-(1-naphthyl)ethyl, or —(CH$_2$)$_p$C$_6$H$_5$;
R$_{11}$ is hydrogen, alkyl of 1 to 6 carbon atoms, cycloalkyl of 3 to 6 carbon atoms, phenyl or benzyl;
R$_{12}$ and R$_{13}$ independently are hydrogen, alkyl of 1 to 4 carbon atoms, phenyl, benzyl, α-methylbenzyl, or taken together form a ring of the formula

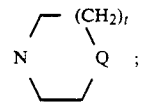

Q is —NR$_{14}$, —O— or —CH$_2$—;
R$_{14}$ and R$_{15}$ are independently hydrogen, alkyl, aryl, aralkyl or cycloalkyl;
R$_{16}$ is C$_{1-6}$alkyl, —NR$_{17}$R$_{18}$ or

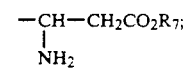

R$_{17}$ and R$_{18}$ are independently hydrogen, C$_{1-6}$alkyl, benzyl or taken together are 3 to 6 carbon atoms forming a 4- to 7-membered ring with the nitrogen atom to which they are attached;
R$_{19}$ is hydrogen, C$_{1-5}$alkyl or phenyl;
R$_{20}$ is —CN, —NO$_2$ or —CO$_2$R$_7$;
Z is —O—, —NR$_6$ or —S—;
m is an integer of 1 to 5;
n is an integer of 1 to 10;
p is 0 or an integer of 1 to 3;
s is 0 or an integer of 1 to 5;
t is 0 or the integer 1; and
Y is —O or —S.
3. A compound of claim 1 wherein
R$_1$ is hydrogen or halogen;
R$_2$ is —CH$_2$OH or —CHO;
R$_3$ is C$_{2-10}$alkyl or C$_{3-10}$alkenyl;
R$_4$ is H or —COOH;
R$_5$ is ortho-tetrazole or COOH;
X is —N— or

and Y is —O—.

4. A compound of formula 2 wherein
R₁ is chloro;
R₂ is —CHO;
R₃ is n-butyl;
connection from the imidazole portion is via the 6-position of the benzoxazole; and
R₅ is ortho-COOH.

5. A compound of claim 2, 2-[6-[(2-Butyl-4-chloro-5-formyl-1H-imidazol-1-yl)methyl]2-benzoxazolyl]benzoic acid, monopotassium salt.

6. A pharmaceutical composition comprising a compound of claim 1 and a pharmaceutically acceptable carrier.

7. A method of treating hypertension comprising administering to a mammalian specie in need thereof a therapeutically effective amount of a composition of claim 6.

8. A method for treating congestive heart failure comprising administering to a mammalian specie in need thereof a therapeutically effective amount of a composition of claim 6.

9. A method for treating cardiac hypertrophy comprising administering to a mammalian specie in need thereof a therapeutically effective amount of a composition of claim 6.

10. A pharmaceutical composition comprising a compound of claim 9 and a pharmaceutically acceptable carrier.

11. A method of treating hypertension comprising administering to a mammalian specie in need thereof a therapeutically effective amount of a composition of claim 10.

12. A method for treating congestive heart failure comprising administering to a mammalian specie in need thereof a therapeutically effective amount of a composition of claim 10.

13. A method for treating cardiac hypertrophy comprising administering to a mammalian specie in need thereof a therapeutically effective amount of a composition of claim 10.

* * * * *

UNITED STATES PATENT AND TRADEMARK OFFICE
CERTIFICATE OF CORRECTION

PATENT NO. : 5,190,942
DATED : March 2, 1993
INVENTOR(S) : Michael A. Poss

It is certified that error appears in the above-identified patent and that said Letters Patent is hereby corrected as shown below:

Column 14, line 8, the word "$R_{12}$" (2nd occurrence) should be --$R_{13}$--.

Column 15, line 45, after the word "hydrogen", delete "-COOR, -$NHSO_2CF_3$".

Column 17, line 2, (in Claim 4), delete the word "formula", and insert in its place the word -- claim --.

Column 18, line 8 (in Claim 10), delete the number "9" and insert in its place the number -- 2 --.

Signed and Sealed this

Sixteenth Day of August, 1994

BRUCE LEHMAN

*Attest:*

*Attesting Officer*          *Commissioner of Patents and Trademarks*